United States Patent
Igarashi et al.

(10) Patent No.: US 10,738,260 B2
(45) Date of Patent: Aug. 11, 2020

(54) FULLERENE DERIVATIVE AND LUBRICANT

(71) Applicant: SHOWA DENKO K.K., Tokyo (JP)

(72) Inventors: Takeshi Igarashi, Tokyo (JP); Kentaro Watanabe, Tokyo (JP); Yasuyuki Ueda, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 57 days.

(21) Appl. No.: 16/322,564

(22) PCT Filed: Aug. 8, 2017

(86) PCT No.: PCT/JP2017/028789
§ 371 (c)(1),
(2) Date: Feb. 1, 2019

(87) PCT Pub. No.: WO2018/030412
PCT Pub. Date: Feb. 15, 2018

(65) Prior Publication Data
US 2019/0203140 A1  Jul. 4, 2019

(30) Foreign Application Priority Data

Aug. 10, 2016 (JP) .................. 2016-158026

(51) Int. Cl.
| | |
|---|---|
| C10M 107/38 | (2006.01) |
| C08G 65/332 | (2006.01) |
| C10M 105/54 | (2006.01) |
| C10N 40/18 | (2006.01) |
| C10N 50/08 | (2006.01) |
| C07C 69/63 | (2006.01) |

(52) U.S. Cl.
CPC .......... *C10M 107/38* (2013.01); *C07C 69/63* (2013.01); *C08G 65/332* (2013.01); *C08G 65/3324* (2013.01); *C10M 105/54* (2013.01); *C10M 2213/0606* (2013.01); *C10N 2040/18* (2013.01); *C10N 2050/08* (2013.01); *Y02P 20/544* (2015.11)

(58) Field of Classification Search
None
See application file for complete search history.

(56) References Cited

U.S. PATENT DOCUMENTS

| | | | | |
|---|---|---|---|---|
| 2002/0031615 | A1* | 3/2002 | Dykes | .................. B82Y 30/00 427/551 |
| 2015/0162044 | A1 | 6/2015 | Hanawa et al. | |
| 2015/0199988 | A1* | 7/2015 | Hanawa | ................ G11B 5/8408 360/75 |
| 2016/0347703 | A1 | 12/2016 | Igarashi et al. | |

FOREIGN PATENT DOCUMENTS

| | | | | |
|---|---|---|---|---|
| JP | 2006-131874 | | 5/2006 | |
| JP | 2006131874 A | * | 5/2006 | ............ B82Y 30/00 |
| JP | 2011-140480 | | 7/2011 | |
| JP | 2013-140923 | | 7/2013 | |
| JP | 2013-170137 | | 9/2013 | |
| JP | 2015-109129 | | 6/2015 | |
| JP | 2015-135710 | | 7/2015 | |
| WO | 2015/125940 | | 8/2015 | |

OTHER PUBLICATIONS

English Machine Translation of JP2006131874 created May 20, 2020. (Year: 2020).*
Bharat Bhushan et al., Sublimed C60 films for tribology, Appl. Phys. Lett. 62, 3253 (1993).
B. M. Ginzburg et al., Antiwear Effect of Fullerene C60 Additives to Lubricating Oils, Russian Journal of Applied Chemistry 75, 1330 (2002).
International Search Report dated Nov. 14, 2017 with respect to PCT/JP2017/028789.

* cited by examiner

*Primary Examiner* — Christopher M Rodd
(74) *Attorney, Agent, or Firm* — IPUSA, PLLC

(57) ABSTRACT

One embodiment of the present invention is a fullerene derivative represented by general formula (1)

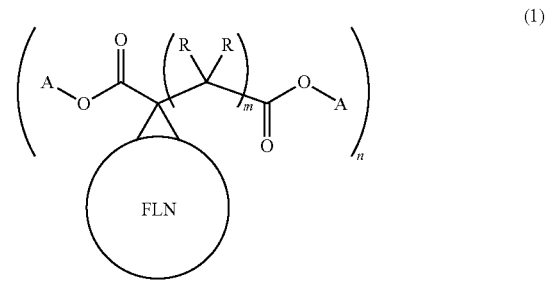

(wherein FLN is a fullerene backbone; each A is independently a monovalent group including a divalent perfluoropolyether group; each R is each independently a hydrogen atom, a hydrocarbon group, or an alkoxycarbonyl group including a divalent perfluoropolyether group; at least one of the 2m R is a hydrocarbon group or an alkoxycarbonyl group including a divalent perfluoropolyether group; m is an integer from 1 to 5; and n is an integer from 1 to 6).

15 Claims, No Drawings

FULLERENE DERIVATIVE AND LUBRICANT

TECHNICAL FIELD

The present invention relates to a fullerene derivative and a lubricant.

BACKGROUND ART

Perfluoropolyether compounds have excellent heat resistance, chemical resistance, and oxidation resistance, and also have a high viscosity index such that they have relatively stable (unchanging) fluidity (viscosity) across a wide temperature range from low temperatures to high temperatures and exhibit good lubricity. Further, perfluoropolyether compounds are nonflammable, have almost no impact on polymer-based materials such as rubber and plastics, and have other characteristics such as low vapor pressure and evaporation loss, low surface tension, and high electrical insulation.

As described above, perfluoropolyether compounds are known to exhibit high performance as a lubricant across an extensively wide range of applications. As such, perfluoropolyether compounds are widely used in vacuum pump oil as lubricating oil, a lubricant for a magnetic disk/tape or the like, a heat medium, a non-adhesive, and various other applications.

On the other hand, $C_{60}$, which is a type of fullerene, is known to be useful as a lubricant.

Non-Patent Literature Document 1 indicates that a silicon substrate having a $C_{60}$ deposited film formed thereon exhibits a lower friction coefficient. Non-Patent Literature Document 1 also describes a fullerene derivative obtained by introducing a perfluoropolyether group into a fullerene. However, the above documents provide no description of specific compounds or their production methods.

Also, $C_{60}$ is known to exhibit excellent properties as an additive to conventional lubricants.

Non-Patent Literature Document 2 indicates measurements of the frictional resistance of a copper foil surface coated with an ordinary lubricating oil and a copper foil surface coated with the lubricating oil that has 5% of $C_{60}$ added thereto. The frictional resistance was measured by rubbing a steel roller while applying a load. The measurement results indicated that the frictional resistance improves when $C_{60}$ is added, as compared with the case where $C_{60}$ is not added.

Patent Document 1 describes a lubricant composed of a mixture of a fullerene, a fullerene derivative having a carboxyl derivative or an ester group of the fullerene, and a perfluoropolyether compound.

Patent Document 2, Patent Document 3, and Patent Document 4 describe a fullerene derivative having one perfluoropolyether group in the molecule as an n-type semiconductor material.

However, Patent Document 2, Patent Document 3 and Patent Document 4 do not describe the application of the fullerene derivative in a lubricant.

Patent Document 5 and Patent Document 6 describe a lubricant composed of a derivative in which one perfluoropolyether group is provided for each cyclopropane ring that is condensed to a fullerene.

Note that owing to the modification of the fullerene, the lubricant described in Patent Documents 5 and 6 exhibit improved abrasion resistance as compared with the lubricant described in Patent Document 1. However, further improvement in abrasion resistance is desirable.

Patent Document 7 describes a lubricant composed of a fullerene derivative in which two perfluoropolyether groups are provided for each cyclopropane ring that is condensed to a fullerene.

As with the lubricant described in Patent Documents 5 and 6, further improvement in abrasion resistance is desirable with respect to the lubricant described in Patent Document 7.

PRIOR ART DOCUMENTS

Patent Documents

Patent Document 1: Japanese Unexamined Patent Publication No. 2006-131874

Patent Document 2: Japanese Unexamined Patent Publication No. 2011-140480

Patent Document 3: Japanese Unexamined Patent Publication No. 2013-140923

Patent Document 4: Japanese Unexamined Patent Publication No. 2013-170137

Patent Document 5: Japanese Unexamined Patent Publication No. 2015-109129

Patent Document 6: Japanese Unexamined Patent Publication No. 2015-135710

Patent Document 7: International Publication No. WO 2015/125940

NON-PATENT LITERATURE DOCUMENTS

Non-Patent Literature Document 1: Appl. Phys. Lett. 62, 3253 (1993)

Non-Patent Literature Document 2: Russian Journal of Applied Chemistry 75, 1330 (2002)

SUMMARY OF THE INVENTION

Problem to be Solved by the Invention

When using a compound including a fullerene backbone as a lubricant, good dispersibility may not be obtained because aggregation of the compound including the fullerene backbone occurs. As a result, the lubricant may not be able to provide sufficient abrasion resistance to an object.

Further, the lubricant according to Patent Document 1 is a mixture of a fullerene or a fullerene derivative and a perfluoropolyether compound, and as such, affinity may be insufficient to prevent aggregation. Thus, even when using a fullerene or a fullerene derivative and a perfluoropolyether compound as a lubricant, sufficient abrasion resistance cannot be provided to an object.

Patent Documents 5 to 7 describe a fullerene derivative that includes a fullerene backbone and a perfluoropolyether group in order to solve the above-described problem.

The perfluoropolyether group included in the fullerene derivative described in Patent Documents 5 to 7 is a part that contributes to solubility in a fluorine-based solvent that is used when coating the lubricant, and also contributes to lubricity itself.

Note that although abrasion resistance can be improved when the fullerene derivative described in Patent Documents 5 to 7 is used, further improvement of abrasion resistance is desirable.

The present invention has been conceived in view of the foregoing problems associated with the prior art, and it is an object of the present invention to provide a fullerene derivative that is capable of improving abrasion resistance of a lubricant.

Means for Solving the Problem

The present invention includes the following embodiments.

[1] A fullerene derivative represented by general formula (1)

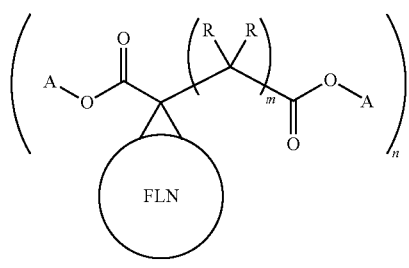

(1)

(wherein FLN is a fullerene backbone; each A is independently a monovalent group including a divalent perfluoropolyether group; each R is independently a hydrogen atom, a hydrocarbon group, or an alkoxycarbonyl group including a divalent perfluoropolyether group; at least one R from among the 2m R is a hydrocarbon group or an alkoxycarbonyl group including a divalent perfluoropolyether group; m is an integer from 1 to 5; and n is an integer from 1 to 6).

[2] The fullerene derivative as described in [1], wherein the fullerene backbone is a $C_{60}$ backbone.

[3] The fullerene derivative as described in [1], wherein at least one R that is bonded to a carbon atom at an α-position of a carbonyl group, from among the 2m R, is a hydrocarbon group or an alkoxycarbonyl group including a divalent perfluoropolyether group.

[4] The fullerene derivative as described in [1], wherein the divalent perfluoropolyether group has at least one partial structure selected from partial structures represented by general formula —$(CF_2)_xO$—

(wherein x is an integer from 1 to 5).

[5] The fullerene derivative as described in [4], wherein the divalent perfluoropolyether group has a partial structure represented by general formula —$(CF_2CF_2O)_y(CF_2O)_z$—

(wherein each of y and z is independently an integer from 1 to 50).

[6] The fullerene derivative as described in [1], wherein the divalent perfluoropolyether group is a straight chain.

[7] The fullerene derivative as described in [1], wherein at least one of the two A and the 2m R includes a non-binding end group that is an aryl group.

[8] The fullerene derivative as described in [7], wherein the two A have non-binding end groups that are aryl groups.

[9] The fullerene derivative as described in [1], wherein m is greater than or equal to 2; and at least one R that is bonded to a carbon atom at a β-position of a carbonyl group, from among the 2m R, is an alkoxycarbonyl group including a divalent perfluoropolyether group.

[10] The fullerene derivative as described in [1] that is represented by general formula (2)

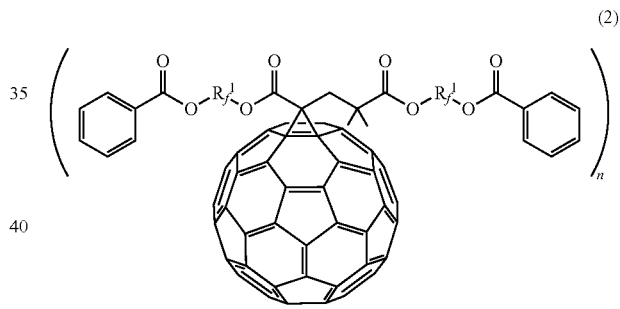

(2)

(wherein $R_f^1$ is a divalent perfluoropolyether group having both ends bonded to methylene groups; and n is 2 or 3).

[11] The fullerene derivative as described in [1] that is represented by general formula (3)

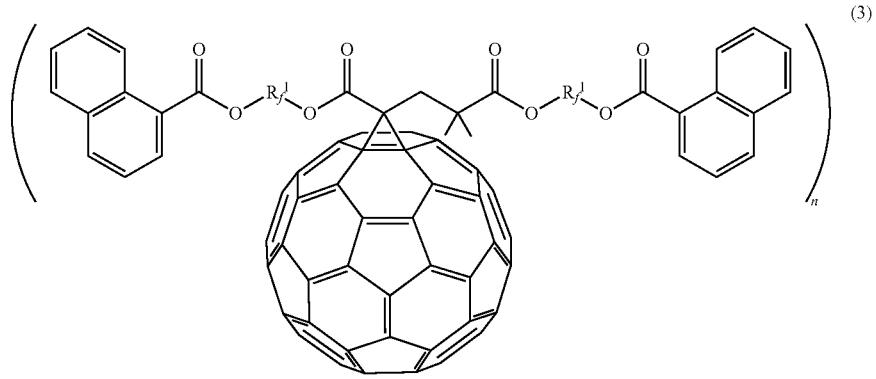

(3)

(wherein $R_f^1$ is a divalent perfluoropolyether group having both ends bonded to methylene groups; and n is from 4 to 6).

[12] The fullerene derivative as described in [1] that is represented by general formula (4)

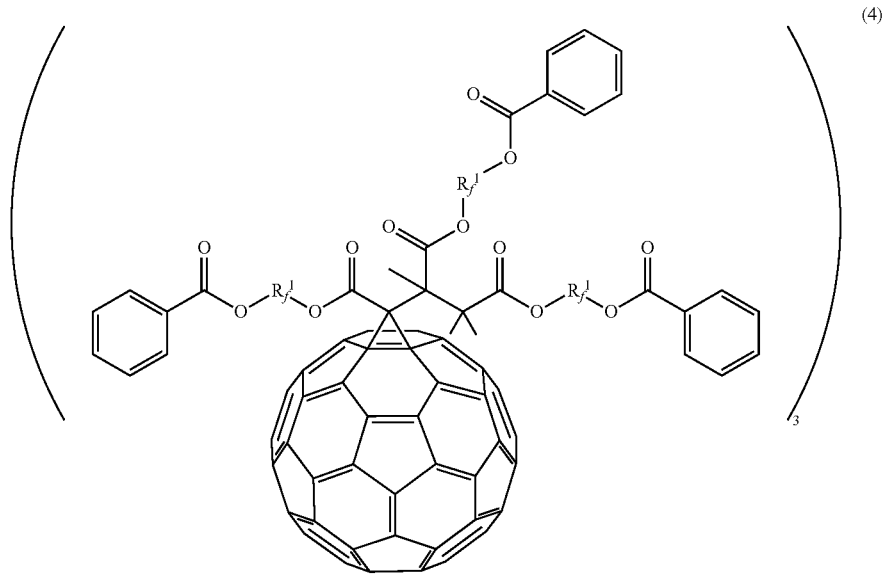

(wherein $R_f^1$ is a divalent perfluoropolyether group having both ends bonded to methylene groups).

[13] A lubricant including the fullerene derivative as described in [1].

Advantageous Effect of the Invention

According to an aspect of the present invention, a fullerene derivative that is capable of improving abrasion resistance of a lubricant can be provided.

EMBODIMENTS FOR IMPLEMENTING THE INVENTION (Fullerene Derivative)

A fullerene derivative according to an embodiment of the present invention is represented by general formula (1)

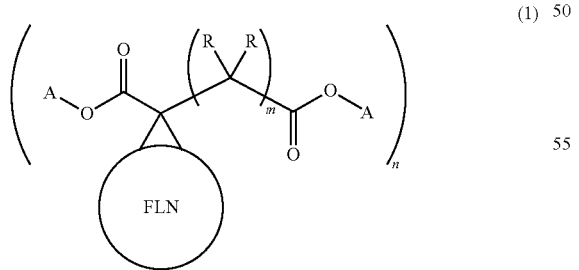

(wherein FLN is a fullerene backbone; each A is independently a monovalent group including a divalent perfluoropolyether group; each R is independently a hydrogen atom, a hydrocarbon group, or an alkoxycarbonyl group including a divalent perfluoropolyether group; at least one R from among the 2m R is a hydrocarbon group or an alkoxycarbonyl group including a divalent perfluoropolyether group; m is an integer from 1 to 5; and n is an integer from 1 to 6).

The fullerene derivative according to the present embodiment includes a fullerene backbone and 1 to 6 cyclopropane rings that are condensed to the fullerene backbone. The cyclopropane ring is bonded to an alkoxycarbonyl group containing a divalent perfluoropolyether group. More specifically, the cyclopropane ring is bonded to an alkoxycarbonyl group containing a divalent perfluoropolyether group via a polymethylene group consisting of m carbon atoms. Further, the m carbon atoms constituting the polymethylene group are only bonded to a hydrogen atom, a hydrocarbon group, or an alkoxycarbonyl group including a perfluoropolyether group, and at least one of the carbon atoms is bonded to at least one hydrocarbon group or at least one alkoxycarbonyl group including a divalent perfluoropolyether group.

The hydrocarbon group represented by R may be, for example, a alkyl group such as a methyl group or an ethyl group, an aryl group such as a phenyl group or a naphthyl group, an aralkyl group such as a benzyl group or a phenylpropyl group, and the like. Among the above examples, an alkyl group or an aryl group is preferable, and a methyl group or a phenyl group is particularly preferable.

The alkoxycarbonyl group including a divalent perfluoropolyether group represented by R in general formula (1) is preferably a group represented by the following general formula:

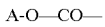

That is, an alkoxy group including a divalent perfluoropolyether group in R is preferably a group represented by the following general formula:

Also, another R that forms a bond with a carbon atom bonded to the alkoxycarbonyl group including a divalent perfluoropolyether group is preferably an alkoxycarbonyl group including a hydrocarbon group or a divalent perfluoropolyether group.

Also, at least one R that forms a bond with a carbon atom at the α-position of a carbonyl group, from among the 2m R, is preferably an alkoxycarbonyl group including a hydrocarbon group or a divalent perfluoropolyether group.

Further, when m is greater than or equal to 2, at least one R that forms a bond with a carbon atom at the β-position of a carbonyl group, from among the 2m R, may be an alkoxycarbonyl group including a divalent perfluoropolyether group.

The divalent perfluoropolyether group preferably has at least one partial structure selected from partial structures represented by the following general formula:

—(CF$_2$)$_x$O—

(wherein, x is an integer from 1 to 5). By including a divalent perfluoropolyether group having such partial structure in the fullerene derivative according to the present embodiment, solubility in a fluorine-based solvent may be improved as compared with a fullerene derivative including a divalent perfluoropolyether group not having such partial structure. As a result, the fullerene derivative may be more evenly coated on a coating surface. Further, from among the compounds having a divalent perfluoropolyether group, a compound having a divalent perfluoropolyether group with the above x being an integer from 1 to 3 may be suitable for industrial applications because such compound is being industrially produced and is readily available.

Further, the divalent perfluoropolyether group more preferably has a partial structure represented by the following general formula:

(CF$_2$CF$_2$O)$_y$(CF$_2$O)$_z$—

(wherein, each of y and z is independently an integer from 1 to 50).

Further, the number average molecular weight of the partial structure represented by the general formula —(CF$_2$CF$_2$O)$_y$(CF$_2$O)$_z$— is preferably in the range from 500 to 6000, and more preferably in the range from 600 to 3000. In this way, the lubricity of the fullerene derivative and the solubility of the fullerene derivative in a fluorine-based solvent may be improved.

Note that the partial structure represented by the general formula

—(CF$_2$)$_x$O— or the partial structure represented by the general formula

—(CF$_2$CF$_2$O)$_y$(CF$_2$O)$_z$— may form a bond with the fullerene backbone via a cyclopropane ring and the like in any orientation.

The divalent perfluoropolyether group is preferably a straight chain.

The structure of the monovalent group including a divalent perfluoropolyether group other than the structure of the divalent perfluoropolyether group is not particularly limited, but for example, the divalent perfluoropolyether group preferably has both ends bonded to methylene groups.

The structure of the alkoxycarbonyl group including a divalent perfluoropolyether group other than the structures of the perfluoropolyether group and the oxycarbonyl group is not particularly limited, but for example, the divalent perfluoropolyether group preferably has both ends bonded to methylene groups.

The non-binding end group of the monovalent group including a perfluoropolyether group; namely, the end group on the opposite side of the end forming a bond with the fullerene backbone via a cyclopropane ring and the like, may be, for example, a perfluoroalkyl group such as a trifluoromethyl group or a perfluoro butyl group, an alkyl group such as a methyl group or a butyl group, an aryl group such as a phenyl group or a naphthyl group, an aralkyl group such as a benzyl group or a phenylpropyl group, an aryloyl group such as a benzoyl group or a naphthoyl group, or the like. Among the above examples, an aryl group is preferable, and an aryloyl group such as a benzoyl group or a naphthoyl group is particularly preferable.

In the fullerene derivative of the present embodiment, at least one of the non-binding end groups of the two A and the 2m R is preferably an aryl group, and more preferably, the non-binding end groups of the two A are aryl groups.

In the general formula (1), A is preferably a group represented by the following general formula:

Ar—COO—CH$_2$-A$^1$-CH$_2$—

(wherein Ar is an aryl group or an aralkyl group, and A$_1$ is a divalent perfluoropolyether group).

The fullerene backbone in the fullerene derivative according to the present embodiment may be, for example, a C$_{60}$ backbone, a C$_{70}$ backbone, a C$_{76}$ backbone, a C$_{78}$ backbone, or a higher order fullerene backbone. Among the above examples, the C$_{60}$ backbone is preferable. Note that it is easier to industrially produce the C$_{60}$ backbone at a higher purity as compared with other fullerene backbones. Thus, the purity of the fullerene derivative that is derived from C$_{60}$ as a raw material may be increased, and the lubricity and smoothness of the fullerene derivative may be improved.

(Lubricant)

A lubricant according to an embodiment of the present invention includes the fullerene derivative according to the present embodiment. The lubricant according to the present embodiment may use the fullerene derivative according to the present embodiment alone, or may have some other lubricant component or an additive generally used as a lubricant added to the fullerene derivative according to the present embodiment to the extent that the effects of the lubricant according to the present embodiment would not be lost or substantially compromised.

The other lubricant component is not particularly limited, but an example thereof includes a perfluoropolyether compound without a fullerene backbone that is conventionally known as a lubricant.

Examples of a perfluoropolyether compound without a fullerene backbone include Fomblin® Series (manufactured by Solvay Specialty Polymers, Inc.) and the like.

The fullerene derivative according to the present embodiment includes a divalent perfluoropolyether group and therefore has high affinity with a perfluoropolyether compound. As such, even when the lubricant according to the present embodiment contains the fullerene derivative according to the present embodiment and a perfluoropolyether compound without a fullerene backbone, the fullerene derivative according to the present embodiment can be uniformly dispersed or dissolved in the perfluoropolyether compound without a fullerene backbone.

Also, in the case where the lubricant according to the present embodiment contains the fullerene derivative according to the present embodiment and a perfluoropolyether compound without a fullerene backbone, the content of the fullerene derivative according to the present embodiment in the lubricant according to the present embodiment is preferably greater than or equal to 0.1 mass % and less than 100 mass %, more preferably greater than or equal to 1 mass % and less than 100 mass %, and more preferably greater than or equal to 10 mass % and less than 100 mass %. In this way, the lubricant according to the present embodiment can exhibit better adhesion to a coated surface.

(Synthesis Method of Fullerene Derivative according to Present Embodiment)

The fullerene derivative according to the present embodiment may be synthesized according to the following synthesis method, for example.

The fullerene derivative represented by the general formula (1) may be synthesized, for example, from a fullerene derivative represented by the following general formula (5)

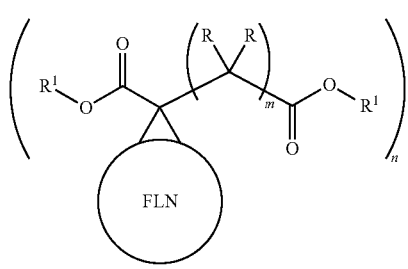

In the above general formula (5), $R^1$ is a methyl group or an ethyl group, and the other symbols represent the same items as those of general formula (1).

The fullerene derivative represented by general formula (5) may be obtained by an addition reaction of a fullerene through addition of an enolate generated by a reaction of an α-halo-ester represented by the following general formula (6) with a base, and a subsequent carbon-carbon bond forming reaction based on nucleophilic attack of a carbanion formed on the fullerene backbone on a carbon atom bonded to a halogen atom.

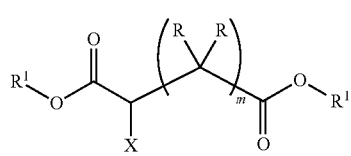

In the above general formula (6), X is a halogen atom, and the other symbols represent the same items as those of general formula (5). Note that when at least one R is an alkoxycarbonyl group including a divalent perfluoropolyether group, the R is preferably a group represented by the following general formula:

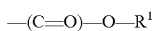

—(C=O)—O—$R^1$

At this time, deprotonation at sites other than where the carbon atom is bonded to the halogen atom is preferably restrained, and in this respect, R that is bonded to a carbon atom at the α-position of a carbonyl group, from among the 2m R included in the α-halo-ester represented by the general formula (6), is preferably a hydrocarbon group or an alkoxycarbonyl group including a divalent perfluoropolyether group.

In the above reaction, generally known bases can be used in the reaction for generating the enolate.

Examples of the base that may be used include sodium hydride, potassium t-butoxide, diazabicycloundecene, and the like.

Also, the above reaction can be carried out in a solvent.

The solvent is not particularly limited as long as it is a solvent capable of dissolving the fullerene, the base, and the α-halo-ester represented by the general formula (6), and examples thereof include toluene, xylene, o-dichlorobenzene (hereinafter also referred to as "ODCB", and the like.

The above reaction is preferably carried out while stirring in an inert gas atmosphere. In this way, generation of by-products can be reduced.

Also, when the reaction rate of the above reaction is slow, heating is preferably performed.

In this case, the heating temperature is preferably less than 180° C. In this way, the occurrence of side reactions may be reduced so that the yield may be improved.

The reaction mixture resulting from the above reaction is neutralized and filtered, after which the reaction solvent is distilled by a rotary evaporator to obtain a crude product.

The crude product includes compounds corresponding to the various values of n for the fullerene derivatives represented by the general formula (5). Note that by purifying the crude product through silica gel column chromatography, the fullerene derivative represented by the general formula (5) can be obtained at a high purity corresponding to one single value or a specific value range of n.

The fullerene derivative represented by the general formula (1) can be obtained by a transesterification reaction of the fullerene derivative represented by the general formula (5) with an alcohol derivative having a divalent perfluoropolyether group in the presence of an acid catalyst.

Note that commonly known organic sulfonic acids can be used as the acid catalyst, and examples thereof include methanesulfonic acid, p-toluenesulfonic acid, trifluoromethanesulfonic acid (hereinafter also referred to as "TfOH"), and the like.

The alcohol derivative having a divalent perfluoropolyether group may be a commercially produced compound such as Fomblin® Series (manufactured by Solvay Specialty Polymers, Inc.), for example.

The above reaction can be carried out in a solvent.

The solvent is not particularly limited as long as it is a solvent capable of dissolving the fullerene derivative represented by the general formula (5) and the alcohol derivative having a divalent perfluoropolyether group.

Examples of the solvent that may be used include mixtures of an aromatic solvent that is capable of dissolving a fullerene derivative, such as toluene, xylene, o-dichlorobenzene, or the like, and a fluorine-based solvent, such as hexafluorobenzene, AK-225 (manufactured by Asahi Glass Co., Ltd.), hexafluorotetrachlorobutane (hereinafter also referred to as "HFTCB"), or the like.

The above reaction is preferably carried out while stirring and heating in an inert gas atmosphere. In this way, generation of by-products can be reduced.

For example, a Soxhlet extractor equipped with a cylindrical filter paper made of glass fiber containing molecular sieves may be used to heat the solvent to a temperature exceeding the boiling point of the solvent. Note that by removing alcohol having a small molecular weight such as methanol that is generated as a by-product by the molecular sieves, the transesterification reaction may be efficiently promoted.

After the reaction mixture resulting from the above reaction is neutralized, the reaction solvent is distilled by a rotary evaporator, after which the resulting mixture is dissolved in a fluorine-based solvent such as AK-225 (manufactured by Asahi Glass Co., Ltd.) and filtered so that impurities such as unreacted fullerene and fullerene derivatives can be removed. Thereafter, the solvent is distilled again to obtain a crude product.

The crude product can be used as a lubricant as is, but when higher purity is required, the crude product can be purified using a carbon dioxide supercritical fluid extraction method, for example. That is, the crude product may be placed in a pressure vessel, and liquefied carbon dioxide may be introduced into the pressure vessel while maintaining the pressure and temperature within the pressure vessel so that the carbon dioxide reaches a supercritical fluid state, and in this way, a target compound may be extracted.

The temperature within the pressure vessel is preferably greater than or equal to 31° C. and less than or equal to 80° C. When the temperature within the pressure vessel is greater than or equal to 31° C., the carbon dioxide may be in a supercritical state, and when the temperature within the pressure vessel is less than or equal to 80° C., the extraction power of the supercritical carbon dioxide may be strengthened.

Also, the pressure within the pressure vessel is preferably greater than or equal to 7.38 MPa and less than or equal to 30 MPa. When the pressure within the pressure vessel is greater than or equal to 7.38 MPa, the carbon dioxide may be in a supercritical state, and when the pressure within the pressure vessel is less than or equal to 30 MPa, the cost of the pressure vessel may be reduced owing to lower pressure resistance performance requirements for the pressure vessel, and as a result, manufacturing costs may be reduced.

Note that when the non-binding end group of the monovalent group including a perfluoropolyether group represented by A in the fullerene derivative represented by the general formula (1) that is obtained by the above-described method is a hydroxy group, a carboxy group, or some other group having a structure that can be converted, the non-binding end group may be converted through known reactions.

The crude product obtained by converting the non-binding end group can be used as is, but when higher purity is required, the crude product may be purified using the carbon dioxide supercritical fluid extraction method, for example.

The lubricant according to the present embodiment may be used as a lubricant for a magnetic recording medium such as a hard disk, for example.

The method for coating the surface of a magnetic recording medium with the lubricant is not particularly limited, but for example, a spin coating method, a dipping method, or the like can be used.

In the case of coating the surface of a magnetic recording medium with the lubricant using the dipping method, for example, the magnetic recording medium may be immersed in a lubricant solution that is contained in an immersion tank of a dip coating apparatus, and the magnetic recording medium may be pulled from the immersion tank at a predetermined speed to form a lubricant layer on the surface of the magnetic recording medium.

The concentration of the fullerene derivative according to the present embodiment in the lubricant solution is preferably greater than or equal to 0.001 mass %, and more preferably greater than or equal to 0.001 mass % and less than 0.1 mass %.

EXAMPLES

In the following, the present invention will be described with respect to specific examples. Note, however, that the present invention is not limited to these examples.

Synthesis Example 1

Synthesis of Compounds 1 to 3:

Dimethyl 1-bromo-3-methyl-1,3-butanedicarboxylate (manufactured by Tokyo Chemical Industry Co., Ltd.) (0.4 g, 1.5 mmol) and $C_{60}$ fullerene (0.36 g, 0.50 mmol) were added to o-dichlorobenzene (40 mL). Then, potassium t-butoxide (0.22 g, 2.0 mmol) was added to the resulting mixture and after stirring the mixture at room temperature for 3 days, the reaction mixture was condensed by a rotary evaporator. Then, the resulting black oily substance was dissolved in an appropriate amount of toluene, filtered, and condensed again by a rotary evaporator to obtain a crude product (0.62 g) as a black solid. The crude product was purified by silica gel column chromatography (developing solvent:toluene-ethyl acetate=100:0 to 9:1). As a result, a fullerene derivative having two cyclopropane rings (Compound 1) as a black solid (94 mg, 86 μmol, yield 17%), a fullerene derivative having three cyclopropane rings (Compound 2) as a black solid (40 mg, 31 μmol, yield 6%), and a fullerene derivative having 4 to 6 cyclopropane rings (Compound 3) as a black solid (132 mg, mixture) were obtained.

Note that Compounds 1 to 3 were identified by mass spectrometry.

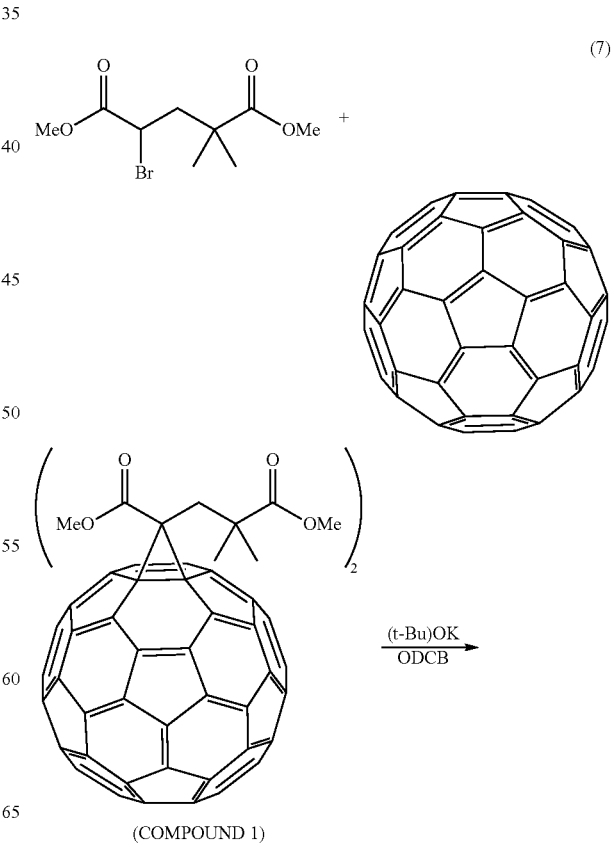

(COMPOUND 1)

-continued

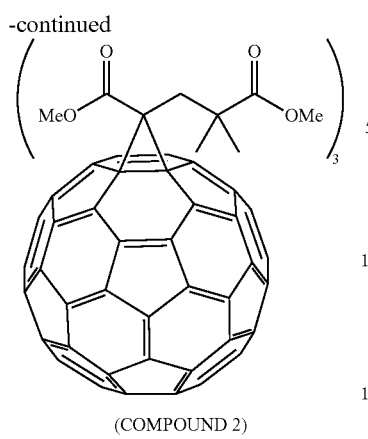

(COMPOUND 2)

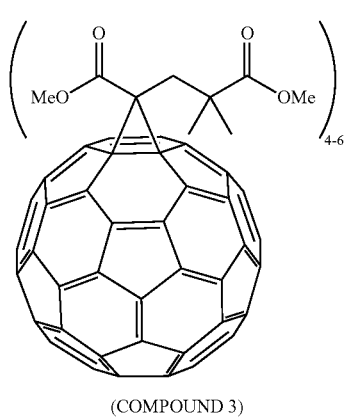

(COMPOUND 3)

Synthesis Example 2

Synthesis of Compound 4:

In an o-dichlorobenzene (25 mL) solution of the Compound 1 (94 mg, 86 μmol) obtained in the above Synthesis Example 1, a hexafluorotetrachlorobutane (25 mL) solution of a perfluoropolyether compound, Fomblin Zdol (manufactured by Solvay Specialty Polymers Co., Ltd.), having a number average molecular weight of about 2000 (2.5 g, 1.3 mmol) was added, after which trifluoromethanesulfonic acid (1 mL) was added dropwise. Then, after installing a Soxhlet extractor equipped with a cylindrical filter paper made of glass fiber containing 4 Å molecular sieves (hereinafter also referred to as "MS4A") and a Dimroth condenser, the mixture was heated in a hot water bath set to 190° C., and refluxed by stirring for 3 hours. The reaction mixture was cooled to room temperature, neutralized by addition of aqueous ammonia (10 mL), and condensed by a rotary evaporator. The obtained oily substance was dissolved in an appropriate amount of a fluorine-based solvent AK-225 (manufactured by Asahi Glass Co., Ltd.), filtered, and condensed by a rotary evaporator to obtain a crude product in the form of black oil (3.2 g).

Then, the crude product was placed in a thick stainless steel pressure vessel (inner diameter 20 mm x depth 200 mm) having an inlet and an outlet, and while maintaining the temperature within the pressure vessel at 60° C., supercritical carbon dioxide was introduced into the pressure vessel at a liquefied carbon dioxide equivalent flow rate of 5 mL/min using a supercritical carbon dioxide liquid feeding pump PU2086-CO2 (manufactured by JASCO Corporation). At this time, the pressure within the pressure vessel was varied within the range from 9 MPa to 17 MPa to remove impurities such as unreacted Fomblin Zdol. Thereafter, the pressure within the pressure vessel was increased to 27 MPa, and 0.22 g of a black solid (Compound 4) was extracted.

(8)

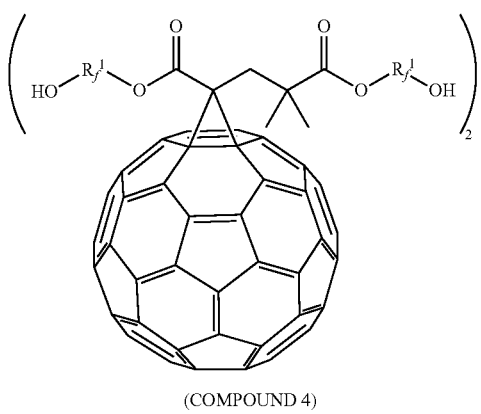

(COMPOUND 1)

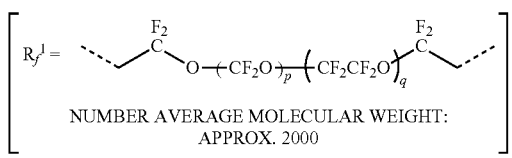

(COMPOUND 4)

[HFTCB = hexafluorotetrachlorobutane]

$$\left[ R_f^1 = \cdots\diagup\diagdown_{C}^{F_2}\diagdown O\text{--}(CF_2O)_p\text{--}(CF_2CF_2O)_q\diagdown_{C}^{F_2}\diagup\cdots \right]$$

NUMBER AVERAGE MOLECULAR WEIGHT: APPROX. 2000

Synthesis Example 3

Synthesis of Compound 5:

The Compound 4 (0.22 g, 25 μmol) obtained in Synthesis Example 2 and triethylamine (23 mg, 0.23 mmol) were added to a fluorine-based solvent AK-225 (manufactured by Asahi Glass Co., Ltd.) (10 mL), and after the mixture was cooled in an ice bath, benzoyl chloride (21 mg, 0.15 mmol) was added. The mixture was returned to room temperature and then stirred for 15 hours. Then, ammonia water (1 mL) was added to the reaction mixture, and the mixture was condensed by a rotary evaporator. The resulting oily substance containing white powder was dissolved in an appropriate amount of tetradecafluorohexane, filtered, and condensed by a rotary evaporator to obtain a crude product (0.20 g) in the form of black oil.

Then, the crude product was placed in a thick stainless steel pressure vessel (inner diameter 20 mm x depth 200 mm) having an inlet and an outlet, and while keeping the temperature within the pressure vessel at 60° C., supercritical carbon dioxide was introduced into the pressure vessel at a liquefied carbon dioxide equivalent flow rate of 5 mL/min using a supercritical carbon dioxide liquid feeding pump PU2086-CO2 (manufactured by JASCO Corporation). At this time, the pressure within the pressure vessel was varied within the range from 10 MPa to 16 MPa, and impurities without a fullerene backbone that could be extracted were removed. Thereafter, the pressure within the pressure vessel was increased to 27 MPa, and 0.14 g of a black solid (Compound 5) was extracted.

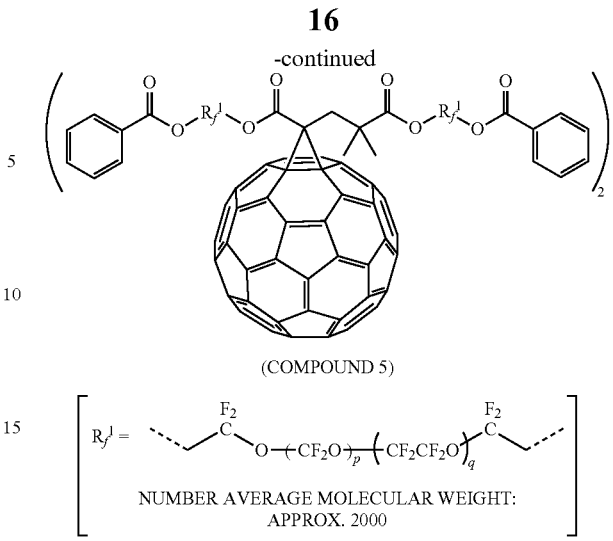

(COMPOUND 5)

$$R_f^1 = \cdots\cdots C_{F_2}O-(CF_2O)_p-(CF_2CF_2O)_q-C_{F_2}\cdots\cdots$$

NUMBER AVERAGE MOLECULAR WEIGHT: APPROX. 2000

Synthesis Example 4

Synthesis of Compound 6:

In an o-dichlorobenzene (25 mL) solution of the Compound 2 (22 mg, 17 μmol) obtained in Synthesis Example 1, a hexafluorotetrachlorobutane (25 mL) solution of a perfluoropolyether compound, Fomblin Zdol (manufactured by Solvay Specialty Polymers), having a number average molecular weight of about 2000 (0.5 mmol) was added, after which trifluoromethanesulfonic acid (0.5 mL) was added dropwise. Then, after installing a Soxhlet extractor equipped with a cylindrical filter paper made of glass fiber containing 4 Å molecular sieves and a Dimroth condenser, the mixture was heated in a hot water bath set to 190° C. and refluxed by stirring for 15 hours. The reaction mixture was cooled to room temperature, neutralized by addition of aqueous ammonia (10 mL), and condensed by a rotary evaporator. The resulting oily substance was dissolved in an appropriate amount of a fluorine-based solvent AK-225 (manufactured by Asahi Glass Co., Ltd.), filtered, and condensed by a rotary evaporator to obtain a crude product in the form of black oil (1.1 g).

Then, the crude product was placed in a thick stainless steel pressure vessel (inner diameter 20 mm x depth 200 mm) having an inlet and an outlet, and while keeping the temperature within the pressure vessel at 60° C., supercritical carbon dioxide was introduced into the pressure vessel at a liquefied carbon dioxide equivalent flow rate of 5 mL/min using a supercritical carbon dioxide liquid feeding pump PU2086-CO2 (manufactured by JASCO Corporation). At this time, the pressure within the pressure vessel was varied within the range from 9 MPa to 16 MPa to remove impurities such as unreacted Fomblin Zdol. Thereafter, the pressure within the pressure vessel was increased to 27 MPa, and 65 mg of a black solid (Compound 6) was extracted.

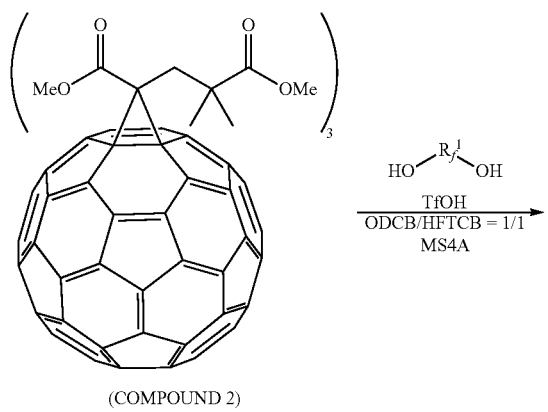

(COMPOUND 2)

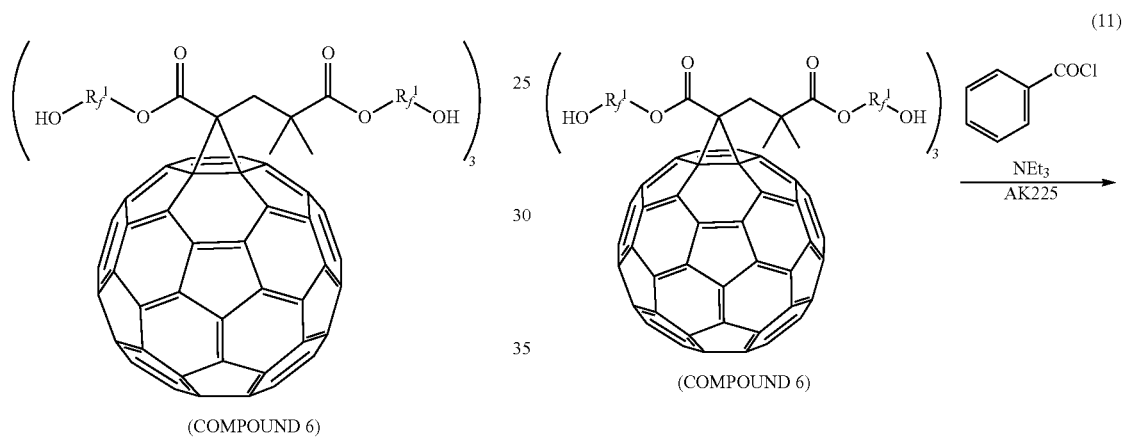

(COMPOUND 6)

[HFTCB = hexafluorotetrachlorobutane]

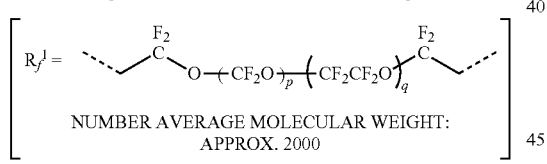

NUMBER AVERAGE MOLECULAR WEIGHT: APPROX. 2000

Synthesis Example 5

Synthesis of Compound 7:

The Compound 6 (65 g, 5.0 μmol) obtained in Synthesis Example 4 and triethylamine (22 mg, 0.22 mmol) were added to a fluorine-based solvent AK-225 (manufactured by Asahi Glass Co., Ltd.) (10 mL), and after cooling the mixture in an ice bath, benzoyl chloride (10 mg, 71 μmol) was added. The mixture was returned to room temperature and then stirred for 15 hours. Then, ammonia water (1 mL) was added to the reaction mixture, and the mixture was condensed by a rotary evaporator. The resulting oily substance containing white powder was dissolved in an appropriate amount of tetradecafluorohexane, filtered, and condensed by a rotary evaporator to obtain a crude product (60 mg) in the form of black oil.

Then, the crude product was placed in a thick stainless steel pressure vessel (inner diameter 20 mm x depth 200 mm) having an inlet and an outlet, and while keeping the temperature within the pressure vessel at 60° C., supercritical carbon dioxide was introduced into the pressure vessel at a liquefied carbon dioxide equivalent flow rate of 5 mL/min using a supercritical carbon dioxide liquid feeding pump PU2086-CO2 (manufactured by JASCO Corporation). At this time, the pressure within the pressure vessel was varied within the range from 10 MPa to 17 MPa, and impurities without a fullerene backbone that could be extracted were removed. Thereafter, the pressure within the pressure vessel was increased to 27 MPa, and 35 mg of a black solid (Compound 7) was extracted.

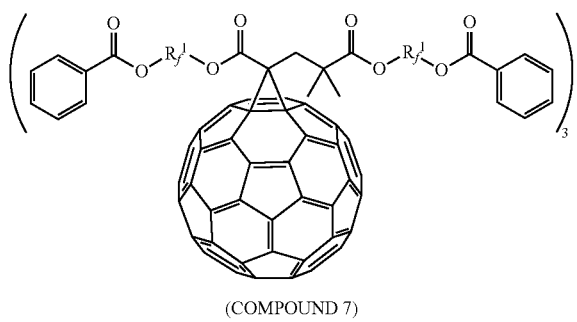

(COMPOUND 7)

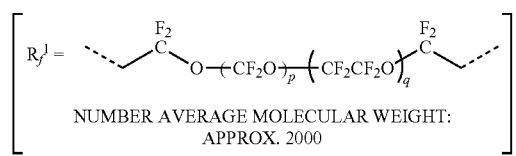

NUMBER AVERAGE MOLECULAR WEIGHT: APPROX. 2000

Synthesis Example 6

Synthesis of Compound 8:

In an o-dichlorobenzene (30 mL) solution of the Compound 3 (0.13 g, mixture) obtained in Synthesis Example 1, a hexafluorotetrachlorobutane (30 mL) solution of a perfluoropolyether compound, Fomblin Zdol (manufactured by Solvay Specialty Polymers Co., Ltd.), having a number average molecular weight of about 2000 (3.6 g, 1.8 mmol) was added, after which trifluoromethanesulfonic acid (1 mL) was added dropwise. Then, after installing a Soxhlet extractor equipped with a cylindrical filter paper made of glass fiber containing 4 Å molecular sieves and a Dimroth condenser, the mixture was heated in a hot water bath set to 190° C. and refluxed by stirring for 3 hours. Then, the reaction mixture was returned to room temperature, neutralized by addition of aqueous ammonia (10 mL), and condensed a rotary evaporator. The resulting oily substance was dissolved in an appropriate amount of a fluorine-based solvent AK-225 (manufactured by Asahi Glass Co., Ltd.), filtered, and condensed by a rotary evaporator to obtain a crude product in the form of black oil (3.6 g).

Then, the crude product was placed in a thick stainless steel pressure vessel (inner diameter 20 mm x depth 200 mm) having an inlet and an outlet, and while keeping the temperature within the pressure vessel at 60° C., supercritical carbon dioxide was introduced into the pressure vessel at a liquefied carbon dioxide equivalent flow rate of 5 mL/min using a supercritical carbon dioxide liquid feeding pump PU2086-CO2 (manufactured by JASCO Corporation). At this time, the pressure within the pressure vessel was varied within the range from 9 MPa to 16 MPa to remove impurities such as unreacted Fomblin Zdol. Thereafter, the pressure within the pressure vessel was increased to 27 MPa, and 0.44 g of a black oily substance (Compound 8) was extracted.

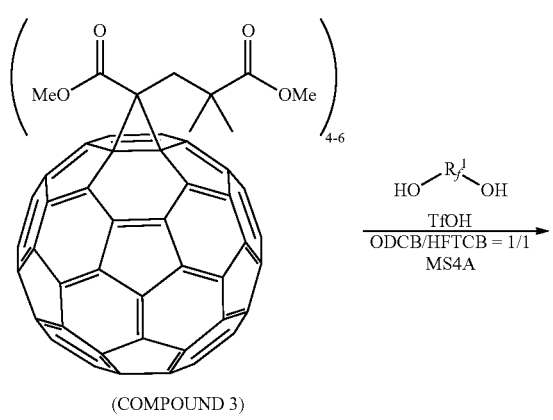

(COMPOUND 3)

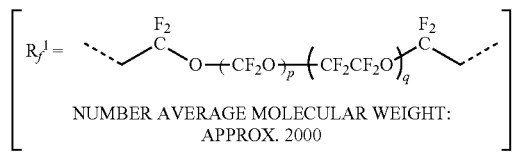

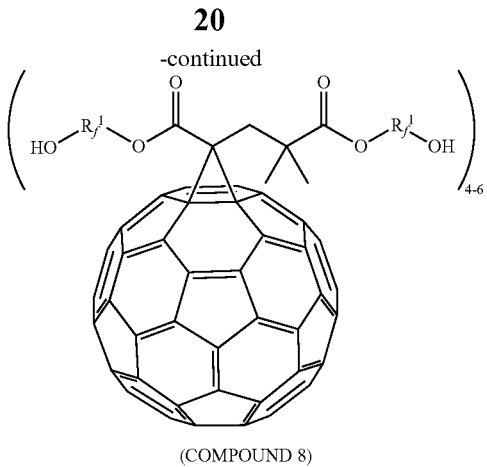

(COMPOUND 8)

[HFTCB = hexafluorotetrachlorobutane]

NUMBER AVERAGE MOLECULAR WEIGHT: APPROX. 2000

Synthesis Example 7

Synthesis of Compound 9:

The Compound 8 (0.19 g) obtained in Synthesis Example 6 and triethylamine (40 mg, 0.40 mmol) were added to a fluorine-based solvent AK-225 (manufactured by Asahi Glass Co., Ltd.) (10 mL), and after cooling the mixture in an ice bath, 1-naphthoyl chloride (43 mg, 2.3 mmol) was added. The mixture was returned to room temperature and then stirred for 15 hours. Then, ammonia water (1 mL) was added to the reaction mixture, and the mixture was condensed by a rotary evaporator. The resulting oily substance containing white powder was dissolved in an appropriate amount of tetradecafluorohexane, filtered, and condensed by a rotary evaporator to obtain a crude product in the form of black oil (91 mg).

Then, the crude product was placed in a thick stainless steel pressure vessel (inner diameter 20 mm x depth 200 mm) having an inlet and an outlet, and while keeping the temperature within the pressure vessel at 60° C., supercritical carbon dioxide was introduced into the pressure vessel at a liquefied carbon dioxide equivalent flow rate of 5 mL/min using a supercritical carbon dioxide liquid feeding pump PU2086-CO2 (manufactured by JASCO Corporation). At this time, the pressure within the pressure vessel was varied within the range from 10 MPa to 17 MPa, and impurities without a fullerene backbone that could be extracted were removed.

Thereafter, the pressure within the pressure vessel was increased to 27 MPa to extract 63 mg of a black solid (Compound 9).

(13)

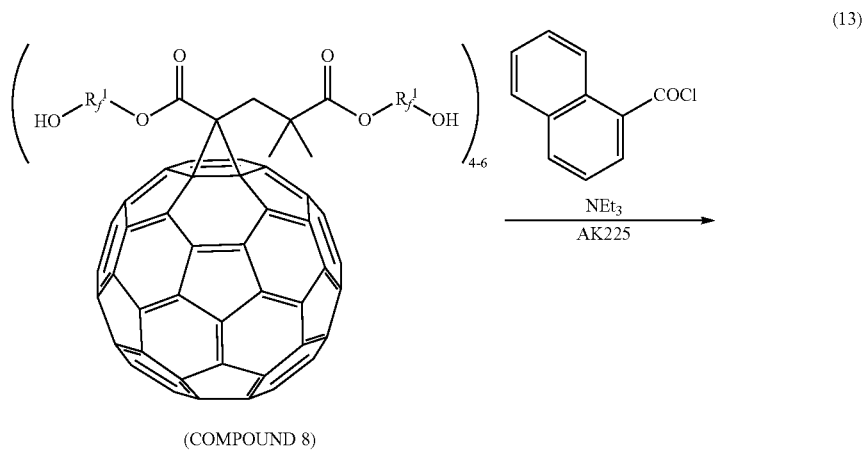

(COMPOUND 8)

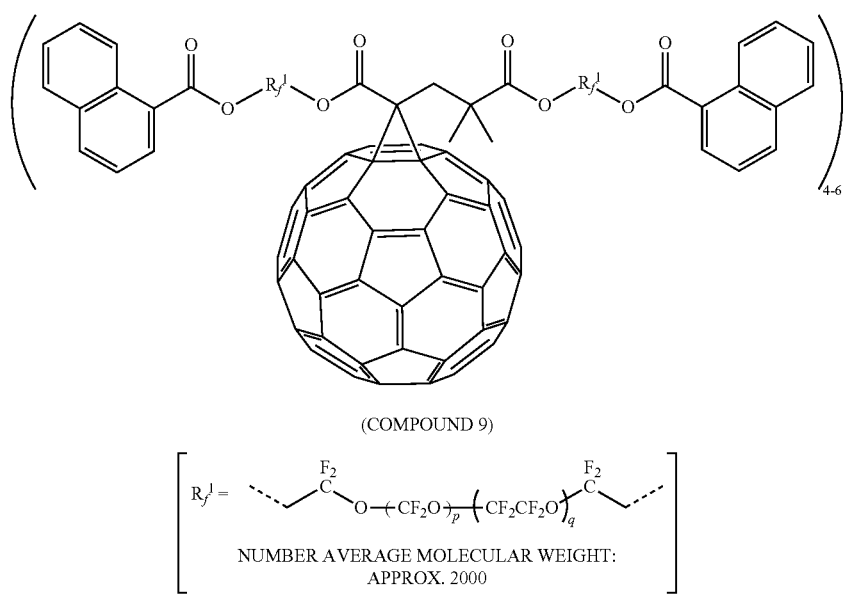

(COMPOUND 9)

$$R_f^1 = \cdots\diagup\overset{F_2}{\underset{}{C}}\diagdown O\text{---}(CF_2O)_p\text{---}(CF_2CF_2O)_q\overset{F_2}{\underset{}{C}}\diagdown\cdots$$

NUMBER AVERAGE MOLECULAR WEIGHT: APPROX. 2000

Synthesis Example 8

Synthesis of Compound 10:

Trimethyl 1-bromo-2,3-dimethyl-1,2,3-butanetricarboxylate (Tokyo Chemical Industry Co., Ltd.) (1.0 g, 3.0 mmol) and sodium hydride (approximately 50% purity, 1.0 g, 21 mmol) was added to toluene (100 mL). $C_{60}$ fullerene (0.73 g, 1.0 mmol) was added to the resulting mixture, and after installing a Dimroth condenser, the mixture was heated in a hot water bath set to 130° C. and refluxed by stirring for 7 days. The reaction mixture was cooled to room temperature, dilute hydrochloric acid (5 mL) was added, and the mixture was condensed by a rotary evaporator. The resulting black oily substance was dissolved in an appropriate amount of toluene, filtered, and condensed again by a rotary evaporator to obtain a crude product (0.72 g) as a black solid. The crude product was purified by silica gel column chromatography (developing solvent:toluene-ethyl acetate=9:1) to obtain a fullerene derivative having three cyclopropane rings (Compound 10) as a black solid (0.23 g, 0.15 mmol, yield 15%).

Note that the Compound 10 was identified by mass spectrometry.

(14)

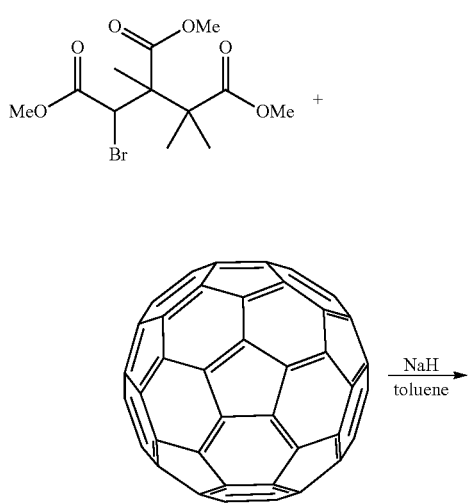

-continued

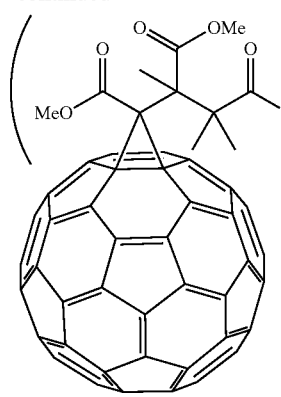

(COMPOUND 10)

Synthesis Example 9

Synthesis of Compound 11:

In an o-dichlorobenzene (60 mL) solution of the Compound 10 (0.23 g, 0.16 mmol) obtained in Synthesis Example 8, a hexafluorotetrachlorobutane (60 mL) solution of a perfluoropolyether compound, Fomblin Zdol (manufactured by Solvay Specialty Polymers Co., Ltd.), having a number average molecular weight of about 2000 (5.7 g, 2.9 mmol) was added, after which trifluoromethanesulfonic acid (1 mL) was added dropwise. Then, after installing a Soxhlet extractor equipped with a cylindrical filter paper made of glass fiber containing 4 Å molecular sieves and a Dimroth condenser, the mixture was heated in a hot water bath set to 190° C. and refluxed by stirring for 5 hours. The reaction mixture was cooled to room temperature, neutralized by addition of aqueous ammonia (10 mL), and condensed by a rotary evaporator. The resulting oily substance was dissolved in an appropriate amount of a fluorine-based solvent AK-225 (manufactured by Asahi Glass Co., Ltd.), filtered, and condensed by a rotary evaporator to obtain a crude product in the form of black oil (5.7 g).

Then, the crude product was placed in a thick stainless steel pressure vessel (inner diameter 20 mm×depth 200 mm) having an inlet and an outlet, and while keeping the temperature within the pressure vessel at 60° C., supercritical carbon dioxide was introduced into the pressure vessel at a liquefied carbon dioxide equivalent flow rate of 5 mL/min using a supercritical carbon dioxide liquid feeding pump PU2086-CO2 (manufactured by JASCO Corporation). At this time, the pressure within the pressure vessel was varied within the range from 10 MPa to 17 MPa to remove impurities such as unreacted Fomblin Zdol. Thereafter, the pressure within the pressure vessel was increased to 27 MPa, and 0.51 g of a black solid (Compound 11) was extracted.

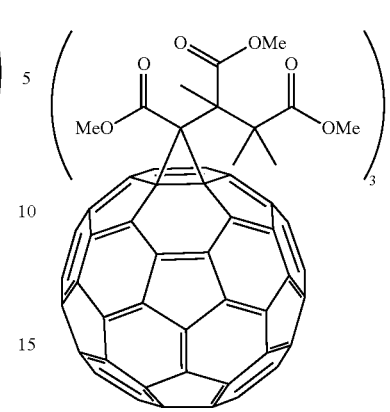

(COMPOUND 10)

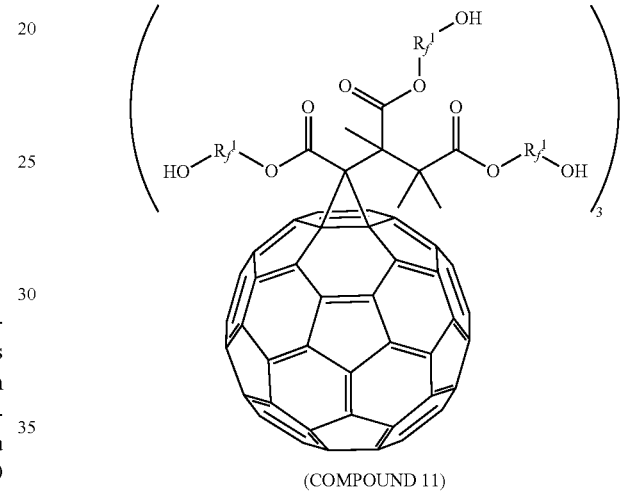

(COMPOUND 11)

[HFTCB = hexafluorotetrachlorobutane]

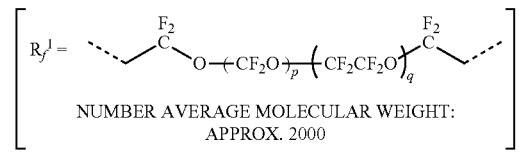

NUMBER AVERAGE MOLECULAR WEIGHT: APPROX. 2000

Synthesis Example 10

Synthesis of Compound 12:

The Compound 11 (0.11 g, 6.0 μmol) obtained in Synthesis Example 9 and triethylamine (22 mg, 0.22 mmol) were added to a fluorine-based solvent AK-225 (manufactured by Asahi Glass Company, Limited) (10 mL), and after cooling the mixture in an ice bath, benzoyl chloride (28 mg, 0.20 mmol) was added. The mixture was returned to room temperature and then stirred for 15 hours. Ammonia water (1 mL) was added to the reaction mixture, and the mixture was condensed by a rotary evaporator. The resulting oily substance containing white powder was dissolved in an appropriate amount of tetradecafluorohexane, filtered, and condensed by a rotary evaporator to obtain a black solid crude product (95 mg).

Then, the crude product was placed in a thick stainless steel pressure vessel (inner diameter 20 mm x depth 200 mm) having an inlet and an outlet, and while keeping the temperature within the pressure vessel at 60° C., supercritical carbon dioxide was introduced into the pressure vessel at a liquefied carbon dioxide equivalent flow rate of 5 mL/min using a supercritical carbon dioxide liquid feeding pump PU2086-CO2 (manufactured by JASCO Corporation). At this time, the pressure within the pressure vessel was varied within the range from 10 MPa to 17 MPa, and impurities without a fullerene backbone that could be extracted were removed. Thereafter, the pressure within the pressure vessel was increased to 27 MPa, and 76 mg of a black solid (Compound 12) was extracted.

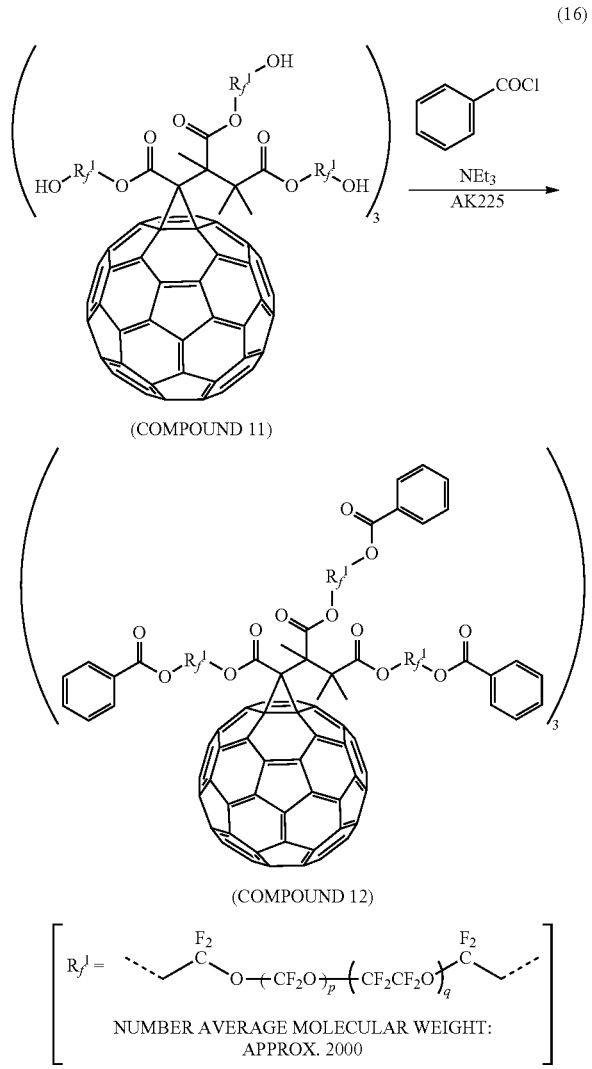

Example 1

A protective layer made of DLC (Diamond-Like Carbon) was formed on a 2.5-inch glass blank for a magnetic disk by high-frequency magnetron sputtering using carbon as a target in an Ar gas atmosphere to produce a simulated disk.

Then, the Compound 5, as a lubricant, was dissolved in tetradecafluorohexane to prepare a 0.001 mass % lubricant solution.

Then, using the dipping method, the lubricant solution was coated onto the protective layer of the simulated disk by the following method. Specifically, the simulated disk was immersed in the lubricant solution contained in an immersion tank of a dip coating apparatus, and the simulated disk was pulled from the immersion tank to coat the surface of the protective layer of the simulated disk with the lubricant solution. Thereafter, the surface coated with the lubricant solution was dried to form a lubricant layer on the protective layer of the simulated disk.

Examples 2 to 4

A lubricant layer was formed on the protective layer of the simulated disk in the same manner as in Example 1 except that the Compound 7, the Compound 9, and the Compound 12 were used in place of the Compound 5.

Comparative Example 1

An attempt was made to form a lubricant layer on the protective layer of the simulated disk in the same manner as in Example 1 except that Compound 13 represented by the following general formula, which is described in Patent Document 5, was used in place of the Compound 5.

(COMPOUND 13)

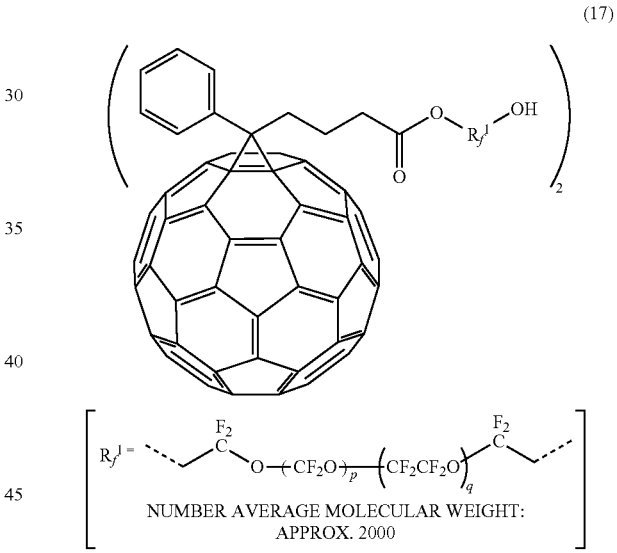

However, because the Compound 13 could not be dissolved in tetradecafluorohexane, a lubricant layer could not be formed.

Comparative Example 2

A lubricant layer was formed on the protective layer of the simulated disk in the same manner as in Comparative Example 1 except that Vertrel® XF (1,1,1,2,3,4,4,5,5,5-decafluoropentane) (manufactured by Mitsui Du Pont Fluorochemicals Co., Ltd.) was used as a solvent.

Comparative Example 3

An attempt was made to form a lubricant layer on the protective layer of the simulated disk in the same manner as in Example 1 except that Compound 14 represented by the following general formula, which is described in Patent Document 7, was used in place of the Compound 5.

(COMPOUND 14)

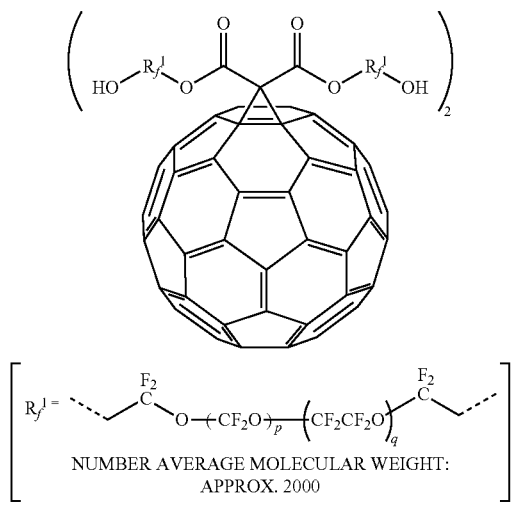

(18)

NUMBER AVERAGE MOLECULAR WEIGHT: APPROX. 2000

However, because the Compound 14 could not be dissolved in tetradecafluorohexane, a lubricant layer could not be formed.

Comparative Example 4

A lubricant layer was formed on the protective layer of the simulated disk in the same manner as in Comparative Example 3 except that Vertrel® XF (1,1,1,2,3,4,4,5,5,5-decafluoropentane) (manufactured by Mitsui Du Pont Fluorochemicals Co., Ltd.) was used as a solvent.

Then, the average film thickness and abrasion resistance of the lubricant layers were evaluated.

(Average Film Thickness of Lubricant Layer)

The film thickness of the lubricant layer was determined from the intensity of the absorption peak corresponding to the stretching vibration energy of a C—F bond in the infrared absorption spectrum, measured using the following measuring apparatus and measurement method. Note that for each lubricant layer, the film thickness was measured at four points, and the average value of the four thickness measurements was obtained as the average film thickness.

Measuring apparatus: Nicolet iS50 (manufactured by Thermo Fisher Scientific)

Measurement method: High sensitivity reflection method (Abrasion Resistance of Lubricant Layer)

The abrasion resistance of the lubricant layer was evaluated using a pin-on-disk frictional wear tester FRICTION PLAYER FRR-2000 (manufactured by RHESCA). A friction and abrasion test was carried out using a 2-mm diameter AlTiC ball as a contact under a load of 40 gf and a sliding speed of 0.25 m/s. As abrasion of the lubricant progresses and the lubricant layer disappears, the contact and the substrate come into contact with each other. As a result, a substantial change in the friction coefficient of the surface of the simulated disk occurs. The time that elapses until a sudden change in the friction coefficient of the surface of the simulated disk occurs is measured as an abrasion resistance evaluation index. For each lubricant layer, the time that elapses until a sudden change in the friction coefficient occurs was measured 4 times, and the average value of the time measurements was used as the abrasion resistance evaluation index of the lubricant layer.

Table 1 shows the average thickness and the abrasion resistance evaluation results of the lubricant layers. Note that the abrasion resistance in Table 1 indicates the time until a sudden change in the friction coefficient occurred.

TABLE 1

| COMPOUND | AVERAGE FILM THICKNESS [nm] | ABRASION RESISTANCE [sec] |
|---|---|---|
| EXAMPLE 1 | COMPOUND 5 | 1.0 | 820 |
| EXAMPLE 2 | COMPOUND 7 | 1.1 | 740 |
| EXAMPLE 3 | COMPOUND 9 | 1.0 | 760 |
| EXAMPLE 4 | COMPOUND 12 | 1.0 | 640 |
| COMPARATIVE EXAMPLE 2 | COMPOUND 13 | 0.9 | 70 |
| COMPARATIVE EXAMPLE 4 | COMPOUND 14 | 1.0 | 150 |

As can be appreciated from Table 1, the time that elapses until a sudden change in the friction coefficient occurs in the lubricant layers of Examples 1 to 5 is longer as compared with the lubricant layers of Comparative Examples 2 and 4 thereby indicating that the lubricant layers of Examples 1 to 5 have higher abrasion resistance.

The present application is based on and claims the benefit of priority of Japanese Patent Application No. 2016-158026 filed on Aug. 10, 2016, the entire contents of which are herein incorporated by reference.

The invention claimed is:

1. A fullerene derivative represented by general formula (1)

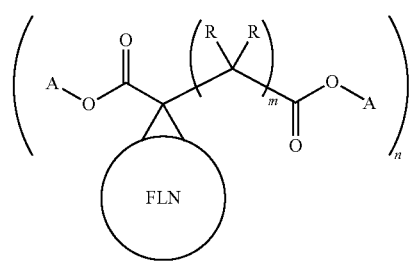

(1)

(wherein FLN is a fullerene backbone; each A is independently a monovalent group including a divalent perfluoropolyether group; each R is independently a hydrogen atom, a hydrocarbon group, or an alkoxycarbonyl group including a divalent perfluoropolyether group; at least one R from among the 2m R is a hydrocarbon group or an alkoxycarbonyl group including a divalent perfluoropolyether group; m is an integer from 1 to 5; and n is an integer from 1 to 6).

2. The fullerene derivative according to claim 1, wherein the fullerene backbone is a $C_{60}$ backbone.

3. The fullerene derivative according to claim 1, wherein at least one R that is bonded to a carbon atom at an α-position of a carbonyl group, from among the 2m R, is a hydrocarbon group or an alkoxycarbonyl group including a divalent perfluoropolyether group.

4. The fullerene derivative according to claim 1, wherein the divalent perfluoropolyether group has at least one partial structure selected from partial structures represented by general formula —$(CF_2)_xO$—

(wherein x is an integer from 1 to 5).

5. The fullerene derivative according to claim 4, wherein the divalent perfluoropolyether group has a partial structure represented by general formula
—(CF$_2$CF$_2$O)$_y$(CF$_2$O)$_z$—
(wherein each of y and z is independently an integer from 1 to 50).

6. The fullerene derivative according to claim 1, wherein the divalent perfluoropolyether group is a straight chain.

7. The fullerene derivative according to claim 1, wherein at least one of the two A and the 2m R includes a non-binding end group that is an aryl group.

8. The fullerene derivative according to claim 7, wherein the two A have non-binding end groups that are aryl groups.

9. The fullerene derivative according to claim 1, wherein m is greater than or equal to 2; and
at least one R that is bonded to a carbon atom at a β-position of a carbonyl group, from among the 2m R, is an alkoxycarbonyl group including a divalent perfluoropolyether group.

10. The fullerene derivative according to claim 1 that is represented by general formula (2)

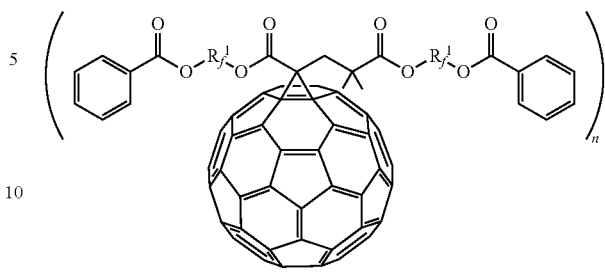

(wherein R$_f^1$ is a divalent perfluoropolyether group having both ends bonded to methylene groups; and n is 2 or 3).

11. The fullerene derivative according to claim 1 that is represented by general formula (3)

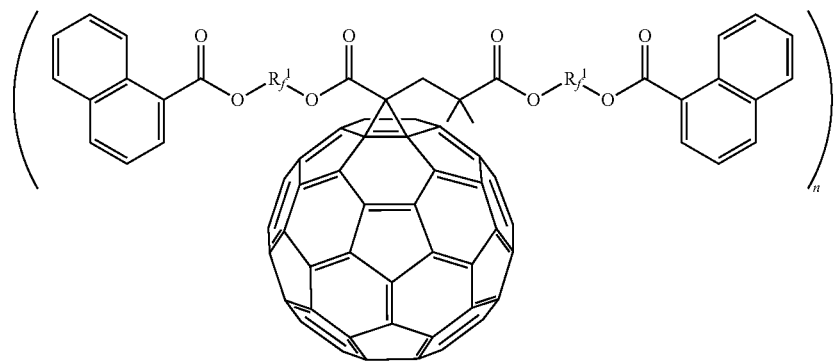

(wherein R$_f^1$ is a divalent perfluoropolyether group having both ends bonded to methylene groups; and n is from 4 to 6).

12. The fullerene derivative according to claim 1 that is represented by general formula (4)

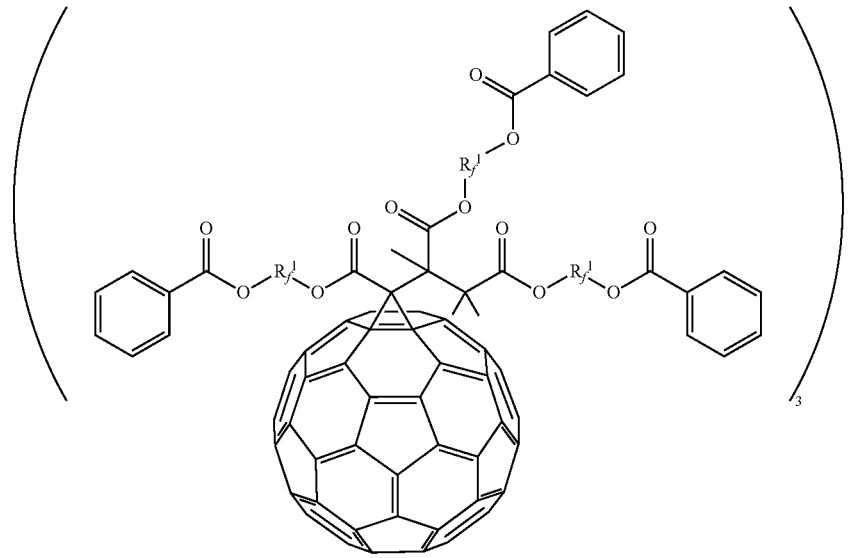

(wherein $R_f^1$ is a divalent perfluoropolyether group having both ends bonded to methylene groups).

13. A lubricant including the fullerene derivative according to claim 1.

14. The fullerene derivative according to claim 1, wherein the fullerene derivative is synthesized from an intermediate compound represented by general formula (5)

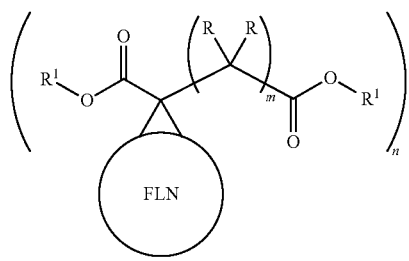

(5)

(wherein FLN is a fullerene backbone; each $R^1$ is independently a methyl group or an ethyl group; each R is independently a hydrogen atom, a hydrocarbon group, or an alkoxycarbonyl group including a divalent perfluoropolyether group; at least one R from among the 2m R is a hydrocarbon group or an alkoxycarbonyl group including a divalent perfluoropolyether group; m is an integer from 1 to 5; and n is an integer from 1 to 6).

15. A fullerene derivative represented by general formula (5)

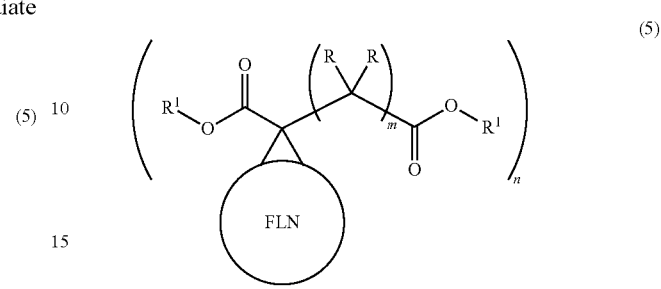

(5)

(wherein FLN is a fullerene backbone; each $R^1$ is independently a methyl group or an ethyl group; each R is independently a hydrogen atom, a hydrocarbon group, or an alkoxycarbonyl group including a divalent perfluoropolyether group; at least one R from among the 2m R is a hydrocarbon group or an alkoxycarbonyl group including a divalent perfluoropolyether group; m is an integer from 1 to 5; and n is an integer from 1 to 6).

* * * * *